United States Patent [19]

Ruschke

[11] Patent Number: 4,966,199

[45] Date of Patent: Oct. 30, 1990

[54] DIAPHRAGM-TYPE CENTER FLOW CHECK VALVE

[75] Inventor: Ricky R. Ruschke, McHenry, Ill.

[73] Assignee: Filtertek, Inc., Hebron, Ill.

[21] Appl. No.: 363,602

[22] Filed: Jun. 8, 1989

[51] Int. Cl.⁵ ............................................. F16K 15/14
[52] U.S. Cl. .................................................. 137/843
[58] Field of Search ............................... 137/843, 854

[56] References Cited

U.S. PATENT DOCUMENTS

| | | |
|---|---|---|
| 1,797,280 | 3/1931 | Zerk . |
| 2,223,944 | 12/1940 | Roy . |
| 3,228,418 | 1/1966 | Rosback et al. . |
| 3,626,978 | 12/1971 | Hoekstra . |
| 3,633,613 | 1/1972 | Julow . |
| 3,661,174 | 5/1972 | Cripe . |
| 3,807,445 | 4/1974 | McPhee . |
| 3,889,710 | 6/1975 | Brost . |
| 3,954,121 | 5/1976 | Kardos . |
| 4,113,627 | 9/1978 | Leason . |
| 4,141,379 | 2/1979 | Manske . |
| 4,190,426 | 2/1980 | Ruschke . |
| 4,210,173 | 7/1980 | Choksi et al. . |
| 4,222,407 | 9/1980 | Ruschke et al. . |
| 4,238,207 | 12/1980 | Ruschke . |
| 4,246,932 | 1/1981 | Raines . |
| 4,286,628 | 9/1981 | Paradis et al. . |
| 4,298,358 | 11/1981 | Ruschke . |
| 4,310,017 | 1/1982 | Raines . |
| 4,369,812 | 1/1983 | Paradis et al. . |
| 4,414,172 | 11/1983 | Leason . |
| 4,415,003 | 11/1983 | Paradis et al. . |
| 4,461,313 | 7/1984 | Beaumont . |
| 4,507,059 | 3/1985 | Kobayashi et al. . |
| 4,518,014 | 5/1985 | McAlpine . |
| 4,535,820 | 8/1985 | Raines . |
| 4,538,508 | 9/1985 | Ballard . |
| 4,550,749 | 11/1985 | Krikorian . |
| 4,610,275 | 9/1986 | Beecher . |
| 4,711,224 | 12/1987 | Eckhardt .................... 137/854 X |
| 4,749,003 | 6/1988 | Leason . |

FOREIGN PATENT DOCUMENTS

| | | |
|---|---|---|
| 0129410 | 12/1984 | European Pat. Off. . |
| 0170007 | 2/1986 | European Pat. Off. . |
| 1387440 | 7/1965 | France . |
| 1600614 | 10/1981 | United Kingdom . |

Primary Examiner—Robert G. Nilson
Attorney, Agent, or Firm—Willian Brinks Olds Hofer Gilson & Lione

[57] ABSTRACT

A center flow check valve of the diaphragm type is inexpensive to manufacture and has reliably great sensitivity in both forward and reverse flow. The valve includes an imperforate diaphragm that is loose, e.g., is not affirmatively held in place by a pin or the like, and the center portion of the diaphragm as well as the periphery move axially in various modes of operation. Various elements help to keep the diaphragm centered. A reverse flow path directs back flow to the center of the downstream surface of the diaphragm. The back flow lifts the diaphragm from support edges about which it flexes during forward flow and seals it against a concave sealing surface. The diaphragm is protected against strong pressure in the forward direction by a flow deflector and against strong back flow pressure by the concave sealing surface. In the absence of forward or backward fluid pressure, the diaphragm assumes a neutral configuration in which it seals against back flow by making line contact with a convex curved surface disposed on the upstream side of the diaphragm.

27 Claims, 2 Drawing Sheets

DIAPHRAGM-TYPE CENTER FLOW CHECK VALVE

BACKGROUND OF THE INVENTION

This invention relates to check-valves and, more particularly, to a center flow check valve of the diaphragm type for use with liquids and gases.

Check valves for a variety of different applications are well known. The purpose of a check valve is to allow fluid flow in one direction only. In the medical field, it is advantageous to include one or more check valves in a tubing set used during intravenous infusion of fluids to a patient. Such fluids often include drugs. It is therefore desirable to limit the size of the check valve in order to minimize the volume of fluid containing the drugs which fills the valve and is generally thrown away with the valve.

Samples of various check valve designs are described in U.S. Pat. No. 4,749,003 of Leason, U.S. Pat. No. 4,222,407 of Ruschke et al, U.S. Pat. No. 3,889,710 of Brost, U.S. Pat. No. 4,415,003 of Paradis et al, U.S. Pat. Nos. 4,246,932, 4,310,017 and 4,535,820 of Raines, and U.S. Pat. No. 4,610,275 of Beecher.

As disclosed in many of these patents, it is very common in a check valve to use a flexible diaphragm (often called a disk) to seal off a flow path through the valve body in order to prevent backflow.

One problem often encountered in using a diaphragm in a check valve is difficulty in keeping the diaphragm properly positioned in relation to the flow path and the sealing surface against which it is to act. One solution to this problem has been to provide a hole in the diaphragm through which a mounting pin extends, holding the disks against transverse movement. Another solution has been to form the pin as a part of the diaphragm and insert the pin into a diaphragm mount during manufacture. In known designs of these types, however, the flow pattern through the valve cannot truly be centered around the diaphragm, because the mounting pin extends in some manner from the central portion of the valve body. In addition, the extra structure represented by the pin and its mounting represents increased material, manufacture and assembly cost. As a class, diaphragm valves suffer from sticking, disk distortion, disk deterioration during use, and improper disk placement.

Another known type of check valve is the duckbill valve, so-called because it includes elements made of silicone rubber that are assembled in opposed fashion so as resemble the bill of a duck (or, more accurately, so as to resemble the reed of a double reed musical instrument). To form the assembly, a member of silicone rubber is folded over to provide a fluid passage, and the fold is cut to provide an exit. Forward flow proceeds from within the assembly through the cut, and back flow tends to press the two members together, closing the opening formed at the cut.

One difficulty of duckbill valves is that the elements, being made of silicone rubber, tend to "heal" or grow together at the cut. This occurrence increases the pressure required to open the valve. Duckbill valves also tend to suffer from incomplete closing against back flow pressure, the result of imperfect cutting during manufacture that removes chunks of silicone. Although both diaphragm type valves and duckbill valves can be very sensitive and operate at low pressures both in the forward flow direction and in the back flow direction, they have not achieved such results consistently. In both cases, pressures required to open the valve, once it begins to malfunction, can typically reach twenty inches of water and can go as high as thirty six inches of water.

SUMMARY OF THE INVENTION

The present invention is directed to a reliably sensitive center flow check valve of the diaphragm type having an axisymmetric flow path and internal structure. The valve includes an imperforate diaphragm that is loose, e.g., is not affirmatively held in place by a pin or the like. The valve body has a number of features that help to keep the diaphragm in its proper concentric position so that it does not become damaged during use or cause a valve malfunction.

A flow deflector directs incoming flow toward the periphery of the diaphragm and away from the center of the diaphragm. The entire periphery of the diaphragm is free to flex about support edges formed on the housing downstream of the diaphragm.

A reverse flow path directs back flow to the center of the downstream surface of the diaphragm. The back flow lifts the diaphragm off the support edges and seals it against a concave sealing surface formed in the inlet portion of the valve body.

The diaphragm is protected against strong pressure in the forward direction by the flow deflector and against strong back flow pressure by a continuous center portion of the concave sealing surface. Nevertheless, the valve is quite sensitive and is reliable in its sensitivity. It can respond to pressures of one or two inches of water, both in the forward and reverse flow directions.

In the absence of forward or backward fluid pressure, the diaphragm assumes a neutral or at rest position in which its upstream surface seals against back flow by making line contact with a convex curved surface disposed just on the upstream side of the diaphragm. In this manner, the valve prevents trickle flow in the reverse direction.

DETAILED DESCRIPTION OF THE DRAWINGS AND OF THE PREFERRED EMBODIMENTS

While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspects of the invention to the embodiment illustrated and described.

Figures 3, 4, 6:
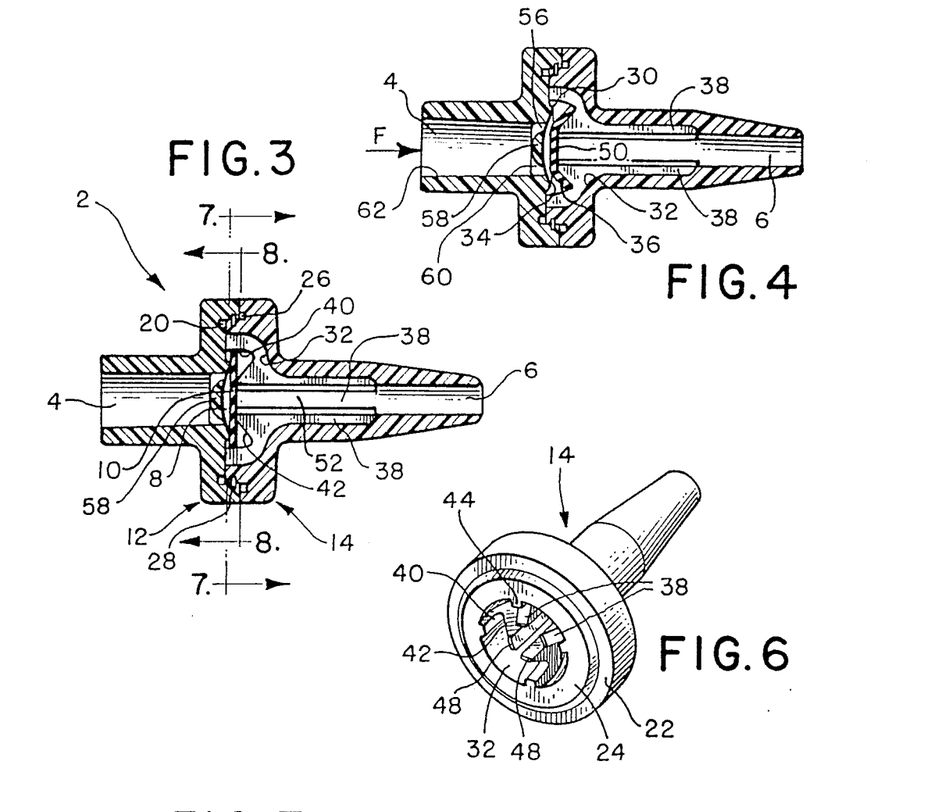
FIG. 3 is an elevational cross-section of a presently preferred embodiment and showing the diaphragm in a neutral configuration in the diaphragm chamber of the valve, the view being taken along the lines 3—3 in FIGS. 2 and 7.
FIG. 4 is a view like that of FIG. 3 but showing the diaphragm in a configuration of flexing about the diaphragm support edges to pass forward flow.
FIG. 6 is a perspective view of the downstream member of the valve housing of the presently preferred embodiment, showing four ribs extending into the downstream portion of the diaphragm chamber.

In a presently preferred embodiment of a check valve according to the current invention, a housing or valve body 2 is provided with an inlet passage 4 and an outlet passage 6 (FIG. 3). In the interior, the valve body 2 is provided with a substantially axisymmetric chamber 8.

A flexible diaphragm 10 is disposed in the chamber 8, as will be described in more detail below. In its presently preferred form, the diaphragm 10 is a disk made of a medical grade silicone rubber material having a durometer of approximately thirty.

The valve body 2 may conveniently be made by molding, and for this purpose may comprise an upstream member 12 and a downstream member 14 fixed together.

Figure 8:
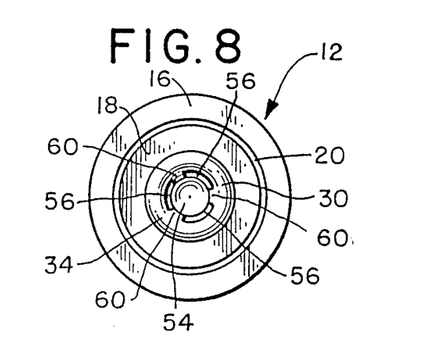
FIG. 8 is an end elevation of the upstream member shown in FIG. 2, taken on line 8 of FIG. 3.

In the illustrated embodiment, the upstream member 12 is provided with an outer flat annular surface 16 (FIG. 8) that is raised above an inner flat annular surface 18. Between these two surfaces lies a first annular flash trap 20.

The downstream member 14 is provided with an inner flat annular surface 24 (FIG. 7) raised above an outer flat annular surface 22 in such a manner that the upstream and downstream members may be mated when sealed, in the manner shown in FIG. 3. Second annular flash trap 26 is formed between the surfaces 22, 24.

The members 12, 14 may be fixed together by ultrasonic welds 28. The flash traps 20, 26 collect melt that is produced during ultrasonic welding. In the alternative, the fixing may be accomplished by adhesive or over-molding techniques as disclosed in U.S. Pat. No. 4,113,627 and 4,414,172, which are hereby incorporated by reference.

The chamber 8 is substantially defined by boundaries thereof, including a cup-shaped surface 32 of downstream member 14 and a concave sealing surface 34 (FIG. 4) of upstream member 12.

FIG. 3 shows the diaphragm 10 in an at rest or neutral configuration. The diaphragm is desirably made of a material that is as soft as possible, provided that the material is not so soft that the diaphragm loses its memory.

In FIG. 3 the memory of the diaphragm causes it to assume a substantially planar shape in which an upstream face 36 (FIG. 4) of the diaphragm makes line contact with an annular convex curved surface 30 (FIGS. 4 and 8) formed on a downstream face of the upstream member 12. Even though the valve is very sensitive in both directions, this line contact forms a seal that helps to prevent even slight back flow through the valve in the reverse direction (shown by the arrow R in FIG. 5) at back-pressures even lower than the sensitivity limit of the valve in the reverse flow direction. Line contact, as opposed to surface contact, maximizes the force of the diaphragm against the surface 30 at low back pressure, insuring no leakage of fluid in the reverse direction.

The above-mentioned line contact when the diaphragm is in an at rest position is desirable but not necessary. Even very slight back flow, when it occurs, will move the diaphragm to the left in FIG. 3 so as to achieve said line contact.

As shown in FIG. 6, a plurality of members in the form of ribs 38 extend radially inwardly from the cup-shaped surface 32. As also shown in FIG. 3, an upstream surface of each rib 38 is dished-out so as to present to the diaphragm 10 an arcuate surface 40 and an angled surface 42 disposed radially inwardly of the arcuate surface 40 and angling inwardly in the upstream direction at a preferred angle of forty five degrees. The resulting configuration may conveniently be thought of as dividing a rib 3B into a first wall 44 (FIGS. 5-7) that bears the arcuate surface 40 and a second wall 46 that bears the angled surface 42 and extends for a substantial distance in the downstream direction.

Figure 5:
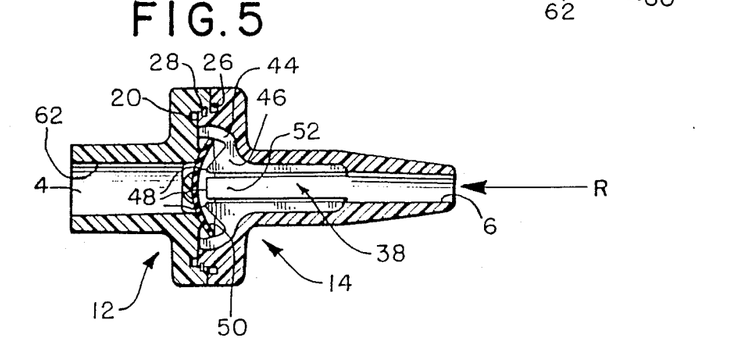
FIG. 5 is a view like that of FIG. 3 but showing the diaphragm in a configuration of responding to back flow pressure and sealing against the concave sealing surface.
Figure 7:
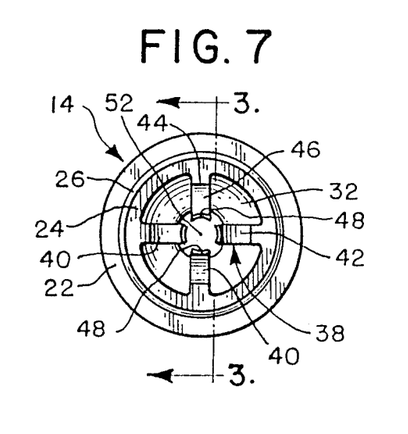
FIG. 7 is an end elevation of the member of FIG. 6, taken on line 7 of FIG. 3 but with the diaphragm removed.

It should be noted from FIG. 7 that, as to the downstream member 14, the cross-section of the FIGS. 3-5 is taken along a plane displaced from the axis of symmetry, so that one views in FIGS. 3-5 the side surfaces of two of the ribs SB and a front surface of a third rib 3B.

The diameter of the diaphragm 10 is just sufficient for it to extend across the chamber 8 from one arcuate surface 40 to an opposite arcuate surface 40. Accordingly, the perimeter of the diagram 10 is displaced radially inwardly from the cup-shaped boundary surface 32 by a distance just greater than the radial dimension of a rib 38 at that point (i.e., of a first wall 44). If one imagines a disk of that diameter placed on FIG. 6, one may realize that four arcuate gaps exist between the edge of the diaphragm 10 and the cup-shaped surface 32, the gaps respectively extending between adjacent pairs of first walls 44.

In the upstream direction, the second walls 46 terminate in means for contacting and supporting the diaphragm 10. In the illustrated embodiment, these take the form of diaphragm contacting surfaces 48 disposed axisymmetrically with respect to the overall flow path through the valve.

In FIG. 4, the arrow F represents downstream, forward flow of the type the valve is designed to pass freely. The axisymmetric contacting surfaces 48 restrain the central portion of the diaphragm 10, while the entire periphery of the diaphragm is free to flex in the downstream direction. With increasing flow, the diaphragm 10 flexes to a greater degree, thereby enlarging the gaps mentioned above between the periphery of the diaphragm and the cup-shaped surface 32.

As shown by arrows in FIG. 4, the incoming fluid passes to the periphery of the diaphragm and around the edges, and then flows through the spaces between the ribs 38 to the outlet passage 6. If the flow rate should become sufficiently great, the portions of the diaphragm that flex eventually will contact the angled surfaces 42. This configuration is shown in FIG. 4.

The diaphragm 10 is imperforate. At no point is it attached to the valve body 2. Accordingly, the illustrated embodiment contains a number of features that help inhibit lateral displacement of the diaphragm 10 that could result in damage to the diaphragm or in failure of the valve. Among these are the arcuate surfaces 40 described above. When the diaphragm 10 is in the neutral configuration shown in FIG. 3 and in the flexed position shown in FIG. 4, the edge of the disk is guided and controlled (but without substantial interference) by the closely proximate arcuate surfaces 40.

According to a further feature of the preferred embodiment, the diaphragm contacting means 48 takes the form of edges that are intentionally made sharp. To form such an edge, each 'rib 38 has a periphery that tapers in the upstream direction and inwardly with respect to the rib.

According to this aspect of the invention, the sharp edges 48 press into the downstream surface 50 of the diaphragm to further inhibit lateral movement of the diaphragm when the diaphragm and the edges 48 are in contact.

In theory, line contact between the diaphragm 10 and the edges 48 is preferred over surface contact. Point contact would be preferred over line contact. It may be seen that, if desired, point contact may be achieved by causing the periphery of each rib to taper to a point rather than to an edge.

Within the limits achievable by molding technology and disk strength, it is thought that smaller areas of contact between a diaphragm and diaphragm support means are preferred over larger areas. In the illustrated embodiment, a diaphragm in the form of a disk may have a diameter of 0.295 inch and a thickness of 0.015 inch. A suitable thickness in the radial direction of a diaphragm contacting surface 48 is 0.005 inch. With current technology, thinner edges are difficult to mold and might cut the diaphragm.

According to a further feature of the current invention, the edges 48 are axisymmetrically disposed about a central reverse flow passage 52 (FIGS. 5 and 7) that is axially continuous with the outlet passage 6. The reverse flow passage 52 is most useful when the valve is operating to halt reverse flow, as represented by the arrow R in FIG. 5.

During reverse flow, the fluid entering outlet passage 6 is not directed to the periphery of the diaphragm in the manner of downstream flow. Instead, reverse flow passage 52 directs this incoming fluid to the center of the downstream surface 50 of the diaphragm, lifting the diaphragm from the edges 48 and pressing it against the upstream boundary of the chamber 8 that is defined by the above-mentioned concave sealing surface 34.

The existence of the open-ended reverse flow passage 52 allows easier molding of the downstream member 14. Also, during molding the steel to make the flow path may act as a support for a center core pin that makes the outlet port.

Preferably, the concave surface 34 is a smooth surface of constant curvature. Most desirably, the contour of the surface 34 is spherical with a radius of 0.110 inch for the diaphragm dimensions specified above.

As shown in FIGS. 3-5 and B, the concave sealing surface 34 extends from the apex of the annular convex curved surface 30 radially inwardly to a continuous portion 54 (FIG. 8) disposed on the axis of the diaphragm, and hence on the axis of the reverse flow passage 52. The concave sealing surface 34 is interrupted by a plurality of communicating openings 56 (FIG'S 2, 4, and 8) that communicate the inlet passage 4 with the chamber B.

The radially outermost portion of the annular convex curved surface 30 may, if desired, have a different radius of curvature than the concave sealing surface 34. However, it is highly desirable for these two arcuate surfaces to meet tangentially. Such meeting should be smooth because it will occur at or near the point of line contact with the diaphragm 10, as shown in FIG. 3.

According to a further aspect of the current invention, the diaphragm 10 responds to reverse fluid flow from the reverse flow passage 52 by conforming to the concave sealing surface 34. In the process, it tightly seals the communicating openings 56, thereby preventing reverse flow through the valve. As the diaphragm 30 changes state from that shown in FIG. 3 to that shown in FIG. 5, it does so in a rolling manner, as the contact between the diaphragm 10 and sealing surface 34 progresses radially inwardly from the line contact of FIG. 3 to the complete surface-to-surface contact of FIG. 5. Both this rolling contact and the concave nature of the sealing surface 34 help to retain the disk in its proper lateral position.

As shown above, the continuous portion 54 of the concave surface 34 is disposed on the upstream side of the diaphragm just opposite the end of the reverse flow passage 52. Therefore, the continuous portion 54 is positioned to serve as a stop for the diaphragm 10 and to resist strong back flow fluid pressures. That is, it prevents strong back flow fluid pressures from blowing the unattached diaphragm down the inlet passage 4.

As shown in FIG. 3, in the illustrated embodiment no flow path exists, not even theoretically, for the leakage of slowly-moving reverse flow through the valve. For this reason, it is preferred for the diaphragm contacting means 48 to be disposed sufficiently far to the left in FIG. 3 that the diaphragm 10, when in the neutral position, is pushed into contact with the annular convex curved surface 30 on the upstream side. However, the valve will function if such contact is not achieved.

According to a further aspect of the current invention, the valve is provided with a flow deflector upstream of and coaxial with the diaphragm B. The flow deflector serves to direct incoming, forward flow represented by the arrow F in FIG. F toward the periphery of the diaphragm and away from the center of the diaphragm. Conveniently, the flow deflector may be incorporated in the same structure that forms the concave sealing surface 34.

Figure 1:
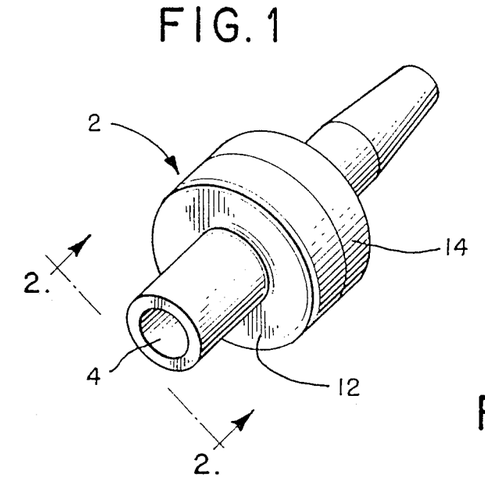
FIG. 1 is a perspective view of an example of an external appearance of a valve according to the current invention and showing upstream and downstream members of a valve housing.
Figure 2:
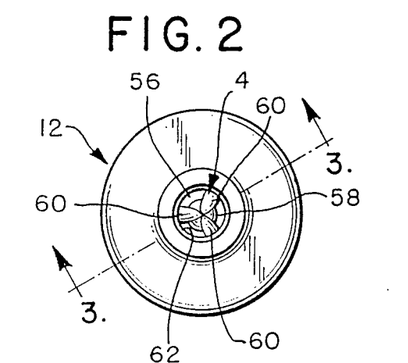
FIG. 2 is an elevation taken along line 2—2 of FIG. 1 and showing a view into the inlet passage of the upstream member of the valve housing of a presently preferred embodiment.

In particular, as shown in FIGS. 2 and 4, a flow deflector 58 has a generally curved, preferably spherical upstream surface and a downstream surface that is the continuous portion 54 of the concave surface 34. The flow deflector 58 is mounted concentrically with respect to the diaphragm 10 by a plurality of support struts 60 that are integrally formed with both the flow deflector 58 and wall 62 of inlet passage 4. Downstream surfaces of the support struts 60 also conveniently form a portion of the concave sealing surface 34.

Because incoming fluid is to be directed to the periphery of the diaphragm during normal downstream flow, use of the fluid deflector assists operation of the valve from a fluid dynamic standpoint In addition, directing incoming fluid to the periphery of the diaphragm before it reaches the diaphragm helps to avoid lateral displacement of the diaphragm. Furthermore, the fluid deflector keeps incoming fluid from impacting the center of the upstream surface of the diaphragm, which, as noted above is disposed opposite to the reverse flow passage 52. Therefore, the fluid deflector keeps the diaphragm from being blown down the reverse flow passage 52 and therefore allows the valve to operate at higher forward flow pressure Moreover, the consequent lower force acting on the center of the disc allows it to bulge when the edges bend.

Of course, variations of the aspects of the invention described above are possible The diaphragm 10 need not be circular For example, a square or star-shaped diaphragm might be used, the extra edges aiding in keeping the diaphragm in position. One might improve performance by making the center of the diaphragm thicker than the periphery, to provide a diaphragm having comparatively more sensitivity relative to its support, stability and strength.

Variations of the current invention are possible in which fewer than all of the above-noted aspects are taken-advantage of. For example, one might mount a diaphragm such that the entire periphery may flex in the downstream direction but without providing for a reverse flow passage 52 or a sealing surface having a concave shape such as surface 34.

The number of ribs 38, four in the drawings, and the number of flow deflector support struts 60 three in the drawings, may be varied as desired. The relative angular position of the ribs 38 and struts 60 about their common axis of symmetry may be selected as desired.

We claim:

1. A check valve for passing fluid flow in a forward direction from an upstream side of the valve to a downstream side, and for preventing fluid flow in a reverse direction, comprising:

a valve body defining a substantially axisymmetric chamber, with internal surfaces of the valve body defining a boundary of the chamber;

an imperforate flexible diaphragm disposed concentrically in the chamber;

the valve body having an inlet passage formed therein in fluid communication with the chamber and extending in the upstream direction from the chamber, the diaphragm being responsive to reverse flow into the chamber for blocking the fluid communication between the chamber and the inlet passage;

the valve body having an outlet passage formed therein extending from the chamber in the downstream direction; and substantially axisymmetric diaphragm contacting means for contacting and supporting a downstream face of the diaphragm during forward flow, said axisymmetric means being spaced radially from the boundary of the chamber and from the periphery of the diaphragm, the axisymmetric means supporting the diaphragm such that the portion of the diaphragm that is disposed radially outwardly of the axisymmetric means may flex in a downstream direction about the axisymmetric means during forward flow to allow for the passage of fluid, the axisymmetric means defining a reverse flow passage for guiding fluid to the center of the downstream face of the diaphragm during reverse flow, the axisymmetric means comprising at least one sharp edge effective to press into the diaphragm and inhibit lateral motion of the diaphragm, the at least one sharp edge being formed on a member disposed in the chamber, the member having a radially inner surface extending in a substantially longitudinal direction along said reverse flow passage to a place where it terminates in said sharp edge, the member further having a radially outer surface tapering inwardly in the upstream direction to a place where it meets said radially inner surface in said sharp edge.

2. The invention of claim 1, comprising a plurality of members disposed in the chamber, the axisymmetric diaphragm contacting means comprising a plurality of said diaphragm contacting surfaces formed on a plurality of said members.

3. The invention of claim 1, comprising a plurality of ribs extending into the chamber from the boundary thereof, the ribs tapering in the upstream direction to a respective plurality of edges, the edges comprising the axisymmetric diaphragm contacting means.

4. The invention of claim 1, comprising a substantially axisymmetric flow deflector disposed in the inlet passage concentrically with respect to the diaphragm, the flow deflector being effective to divert forwardly flowing fluid toward the periphery of an upstream face of the diaphragm and substantially away from that portion of the diaphragm that is opposite the reverse flow passage.

5. The invention of claim 1, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber.

6. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the chamber;

an imperforate flexible diaphragm disposed concentrically in the chamber;

a valve body having an inlet passage formed therein in fluid communication with the chamber and extending in the upstream direction from the chamber, the diaphragm being responsive to reverse flow into the chamber for blocking said fluid communication between the chamber and the inlet passage;

the valve body having an outlet passage formed therein and extending from the chamber in the downstream direction; and a plurality of members disposed in the chamber and tapering to a respective plurality of edges, the members having radially inner surfaces extending in a substantially longitudinal direction and terminating in said edges, the members further having radially outer surfaces tapering inwardly in the upstream direction and meeting said radially inner surfaces in said edges, the edges contacting and supporting a downstream face of the diaphragm during forward flow, the edges being spaced radially from the boundary of the chamber and from the periphery of the diaphragm, the edges supporting the diaphragm such that the portion of the diaphragm that is disposed radially outwardly of the edges may flex in a downstream direction about the edges during forward flow to allow for the passage of fluid, the edges being so disposed and sufficiently sharp in relation to the diaphragm that they comprise may inhibiting lateral motion of the diaphragm.

7. The invention of claim 6, comprising a plurality of ribs extending into the chamber from the boundary thereof, the ribs tapering in the upstream direction to form the edges.

8. The invention of claim 6, the edges defining a passage for guiding fluid to the center of the downstream face of the diaphragm during reverse flow.

9. The invention of claim 6, comprising a substantially axisymmetric flow deflector disposed in the inlet passage concentrically with respect to the diaphragm, the flow deflector being effective to divert forwardly flowing fluid toward the periphery of an upstream face of the diaphragm.

10. The invention of claim 6, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber.

11. A check valve for passing fluid flow in a forward direction from an upstream inlet side of the valve to a downstream outlet side, and for preventing fluid flow in a reverse direction, comprising:

a valve body defining a substantially axisymmetric chamber, internal surfaces of the valve body defining a boundary of the chamber;

an imperforate flexible diaphragm disposed concentrically in the chamber;

a valve body having an inlet passage formed therein in fluid communication with the chamber and extending in the upstream direction from the chamber, the diaphragm being responsive to reverse flow into the chamber for blocking the fluid communication between the chamber and the inlet passage;

the valve body having an outlet passage formed therein and extending from the chamber in the downstream direction;

diaphragm contacting means for contacting and supporting a downstream side of the diaphragm during forward flow, the diaphragm contacting means supporting the diaphragm such that the diaphragm may flex in a downstream direction during forward flow to allow for the passage of fluid, the diaphragm contacting means defining an end of a reverse flow passage for guiding fluid to the center of a downstream face of the diaphragm during reverse flow; and a substantially axisymmetric flow deflector disposed in the inlet passage concentrically with respect to the diaphragm, the flow deflector being effective to divert forwardly flowing fluid toward the periphery of an upstream face of the diaphragm and substantially away from that portion of the diaphragm that is opposite the reverse flow passage.

12. The invention of claim 11, comprising a plurality of members tapering to a respective plurality of edges, the edges comprising the diaphragm contacting means.

13. The invention of claim 11, comprising a plurality of ribs disposed in the chamber and tapering in the upstream direction to a respective plurality of edges, the edges comprising the diaphragm contacting means.

14. The invention of claim 11, the boundary of the chamber including a concave surface disposed upstream of the diaphragm and substantially concentric with respect to the diaphragm, the concave surface having a plurality of communicating openings formed therein, a portion of the concave surface that is coaxially with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber.

15. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the diaphragm chamber;

a diaphragm comprising an imperforate flexible disc disposed concentrically in the chamber;

a valve body having inlet and outlet passages formed therein respectively extending upstream from and downstream from the chamber; and diaphragm contacting means for contacting and supporting a downstream face of the diaphragm during forward flow, the boundary of the chamber including a concave surface disposed upstream of the diaphragm, spaced from an upstream surface of the diaphragm, and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber, and a plurality of members tapering to a respective plurality of edges, the edges comprising the diaphragm contacting means.

16. The invention of claim 15, there being an annular convex curved surface disposed concentrically of and radially beyond the concave surface, an upstream face of the diaphragm making line contact with the convex surface under slight reverse pressure.

17. The invention of claim 16, there being a smooth transition between the convex surface and the concave surface, the diaphragm rolling along the convex surface under increasing reverse pressure until it lies flush against the concave surface.

18. The invention of claim 15, comprising a substantially axisymmetric flow deflector disposed in the inlet passage concentrically with respect to the diaphragm, said flow deflector being effective to divert forwardly flowing fluid toward the periphery of an upstream face of the diaphragm, a downstream face of the flow deflector defining at least a portion of the concave surface.

19. The invention of claim 15, the plurality of members comprising a plurality of ribs disposed in the chamber and tapering in the upstream direction to a respective plurality of edges, the edges comprising the diaphragm contacting means.

20. A check valve for passing fluid flow in a forward direction from an upstream side of the valve to a downstream side, and for preventing fluid flow in a reverse direction, comprising:

a valve body defining s substantially axisymmetric chamber, with internal surfaces of the valve body defining a boundary of the chamber;

an imperforate flexible diaphragm disposed concentrically in the chamber;

the valve body having an inlet passage formed therein in fluid communication with the chamber and extending in the upstream direction from the chamber, the diaphragm being responsive to reverse flow into the chamber for blocking the fluid communication between the chamber and the inlet passage;

the valve body having an outlet passage formed therein extending from the chamber in the downstream direction;

substantially axisymmetric diaphragm contacting means for contacting and supporting a downstream face of the diaphragm during forward flow, said axisymmetric means being spaced radially from the boundary of the chamber and from the periphery of the diaphragm, the axisymmetric means supporting the diaphragm such that the portion of the diaphragm that is disposed radially outwardly of the axisymmetric means may flex in a downstream direction about the axisymmetric means during forward flow to allow for the passage of fluid, the axisymmetric means defining a reverse flow passage for guiding fluid to the center of the downstream face of the diaphragm during reverse flow; and a substantially axisymmetric flow deflector disposed in the inlet passage concentrically with respect to the diaphragm, the flow deflector being effective to divert forwardly flowing fluid toward the periphery of an upstream face of the diaphragm and substantially away from that portion of the diaphragm that is opposite the reverse flow passage.

21. A check valve for passing fluid flow in a forward direction from an upstream side of the valve to the downstream side, and for preventing fluid flow in a reverse direction, comprising:

a valve body defining a substantially axisymmetric chamber, with internal surfaces of the valve body defining a boundary of the chamber;

an imperforate flexible diaphragm disposed concentrically in the chamber;

the valve body having an inlet passage formed therein in fluid communication with the chamber and extending in the upstream direction from the chamber, the diaphragm being responsive to reverse flow into the chamber for blocking the fluid communication between the chamber and the inlet passage;

the valve body having an outlet passage formed therein extending from the chamber in the downstream direction, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free to the communicating openings, the inlet passage being in fluid communication with the chamber through the communicating openings in the concave surface, the diaphragm being disposed for flexing and sealing against the concave surface and blocking the communicating openings in response to reverse flow into the chamber; and substantially axisymmetric diaphragm contacting means for contacting and supporting a downstream face of the diaphragm during forward flow, said axisymmetric means being spaced radially from the boundary of the chamber and from the periphery of the diaphragm, the axisymmetric means supporting the diaphragm such that the portion of the diaphragm that is disposed radially outwardly of the axisymmetric means may flex in a downstream direction about the axisymmetric means during forward flow to allow for the passage of fluid, the axisymmetric means defining a reverse flow passage for guiding fluid to the center of the downstream face of the diaphragm during reverse flow.

22. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the chamber;

an imperforate flexible diaphragm disposed concentrically in the chamber;

a valve body having an inlet passage formed therein in fluid communication with the chamber and extending in the upstream direction from the chamber, the diaphragm being responsive to reverse flow into the chamber for blocking said fluid communication between the chamber and the inlet passage;

the valve body having an outlet passage formed therein and extending from the chamber in the downstream direction;

a plurality of members disposed in the chamber and tapering to a respective plurality of edges, the edges contacting and supporting a downstream face of the diaphragm during forward flow, the edges being spaced radially from the boundary of the chamber and from the periphery of the diaphragm, the edges supporting the diaphragm such that the portion of the diaphragm that is disposed radially outwardly of the edges may flex in a downstream direction about the edges during forward flow to allow for the passage of fluid; and a substantially axisymmetric flow deflector disposed in the inlet passage concentrically with respect to the diaphragm, the flow deflector being effective to divert forwardly flowing fluid toward the periphery of an upstream face of the diaphragm.

23. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the chamber;

an imperforate flexible diaphragm disposed concentrically in the chamber;

a valve body having an inlet passage formed therein in fluid communication with the chamber and extending in the upstream direction from the chamber, the diaphragm being responsive to reverse flow into the chamber for blocking said fluid communication between the chamber and the inlet passage;

the valve body having an outlet passage formed therein and extending from the chamber in the downstream direction, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber; and a plurality of members disposed in the chamber and tapering to a respective plurality of edges, the edges contacting and supporting a downstream face of the diaphragm during forward flow, the edges being spaced radially from the boundary of the chamber and from the periphery of the diaphragm, the edges supporting the diaphragm such that the portion of the diaphragm that is disposed radially outwardly of the edges may flex in a downstream direction about the edges during forward flow to allow for the passage of fluid.

24. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the diaphragm chamber;

an imperforate flexible diaphragm disposed concentrically in the chamber;

a valve body having inlet and outlet passages formed therein respectively extending upstream from and downstream from the chamber; and diaphragm contacting means for contacting and supporting a downstream face of the diaphragm during forward flow, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber, there being an annular convex curved surface disposed concentrically of and radially beyond the concave surface, an upstream face of the diaphragm making line contact with the convex surface under slight reverse pressure.

25. The invention of claim 24, there being a smooth transition between the convex surface and the concave surface, the diaphragm rolling along the convex surface under increasing reverse pressure until it lies flush against the concave surface.

26. A check valve for passing fluid flow in a forward direction from an upstream inlet side of the valve to a downstream outlet side, and for preventing fluid flow in a reverse direction, comprising:

a valve body defining a substantially axisymmetric chamber, with internal surfaces of the valve body defining a boundary of the diaphragm chamber;

an imperforate flexible diaphragm disposed concentrically in the chamber;

a valve body having inlet and outlet passages formed therein respectively extending upstream from and downstream from the chamber; and a plurality of members tapering to a respective plurality of edges, the edges comprising means for contacting and supporting a downstream face of the diaphragm during forward flow, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber.

27. A check valve for passing fluid flow in a forward direction from an upstream inlet side of the valve to a downstream outlet side, and for preventing fluid flow in a reverse direction, comprising:

a valve body defining a substantially axisymmetric chamber, internal surfaces of the valve body defining a boundary of the diaphragm chamber;

an imperforate flexible diaphragm disposed concentrically in the chamber;

a valve body having inlet and outlet passages formed therein respectively extending upstream from and downstream from the chamber; and a plurality of ribs disposed in the chamber and tapering in the upstream direction to a respective plurality of edges, the edges comprising means for contacting and supporting a downstream face of the diaphragm during forward flow, the boundary of the chamber including a concave surface disposed upstream of the diaphragm and substantially concentric with respect to the diaphragm, the concave surface having a plurality of communicating openings formed therein, a portion of the concave surface that is coaxial with the diaphragm being continuous and free of the communicating openings, the inlet passage being in fluid communication with the chamber through the communicating openings in the concave surface, the diaphragm being disposed for flexing and sealing against the concave surface and blocking the communicating openings in response to reverse flow into the chamber.

* * * * *

UNITED STATES PATENT AND TRADEMARK OFFICE
CERTIFICATE OF CORRECTION

PATENT NO.  : 4,966,199
DATED       : October 30, 1990
INVENTOR(S) : Ricky R. Ruschke It is certified that error appears in the above-identified patent and that said Letters Patent is hereby corrected as shown below:

In column 1, line 16, please delete "volumn" and substitute therefor --volume--.

In column 1, line 50, before "resemble" please insert --to--.

In column 4, line 21, please delete "3B" and substitute therefor --38--.

In column 4, line 29, please delete "SB" and substitute therefor --38--; and delete "3B" and substitute therefor --38--.

In column 4, line 33, please delete "diagram" and substitute therefor --diaphragm--.

In column 5, line 60, please delete "B" and substitute therefor --8--.

In column 5, line 68, please delete "B" and substitute therefor --8--.

In column 6, line 41, please delete "B" and substitute therefor --8--.

UNITED STATES PATENT AND TRADEMARK OFFICE
CERTIFICATE OF CORRECTION

PATENT NO. : 4,966,199

DATED : October 30, 1990

INVENTOR(S) : Ricky R. Ruschke

It is certified that error appears in the above-identified patent and that said Letters Patent is hereby corrected as shown below:

In column 6, line 43, please delete the second occurrence of "F" and substitute therefor --4--.

In column 6, line 61, after "standpoint" please insert --.--.

In column 7, line 7, after "possible" please insert --.--.

In column 7, line 8, after "circular" please insert --.--.

IN THE CLAIMS

Col. 9, In claim 6, line 6, please delete "may" and substitute therefor --means--.

Col. 12, In claim 21, line 10, please delete "to" and substitute therefor --of--.

Signed and Sealed this

Twenty-fourth Day of November, 1992

*Attest:*

DOUGLAS B. COMER

*Attesting Officer*     *Acting Commissioner of Patents and Trademarks*